United States Patent
Zamora et al.

(10) Patent No.: US 8,392,121 B2
(45) Date of Patent: Mar. 5, 2013

(54) SYSTEM AND METHOD OF ANALYZING FLUIDS AT A DRILLING LOCATION

(75) Inventors: Mario Zamora, Houston, TX (US); Tore Stock, Kleppe (NO)

(73) Assignees: M-I L.L.C., Houston, TX (US); Schlumberger Norge AS, Tananger (NO)

( * ) Notice: Subject to any disclaimer, the term of this patent is extended or adjusted under 35 U.S.C. 154(b) by 309 days.

(21) Appl. No.: 12/739,578

(22) PCT Filed: Oct. 24, 2008

(86) PCT No.: PCT/US2008/081114
§ 371 (c)(1),
(2), (4) Date: Apr. 23, 2010

(87) PCT Pub. No.: WO2009/055672
PCT Pub. Date: Apr. 30, 2009

(65) Prior Publication Data
US 2010/0250142 A1 Sep. 30, 2010

Related U.S. Application Data

(60) Provisional application No. 60/982,805, filed on Oct. 26, 2007.

(51) Int. Cl.
*G01N 15/08* (2006.01)
*G06F 19/00* (2011.01)
(52) U.S. Cl. ............... 702/12; 73/152.19; 702/50
(58) Field of Classification Search ............... 702/6, 9, 702/12, 45, 130, 183, 188, 50; 73/152.19, 73/152.23; 166/250.01, 264, 311; 210/739; 507/103, 240
See application file for complete search history.

(56) References Cited

U.S. PATENT DOCUMENTS

| | | | |
|---|---|---|---|
| 3,286,510 A | 11/1966 | Parker | |
| 4,557,142 A * | 12/1985 | Hensley et al. | 73/152.19 |
| 7,521,400 B2 * | 4/2009 | Samuel | 507/240 |
| 7,677,307 B2 * | 3/2010 | Vasques et al. | 166/264 |
| 7,736,521 B2 * | 6/2010 | Sloan et al. | 210/739 |
| 2009/0049904 A1 * | 2/2009 | Meister | 73/152.23 |

FOREIGN PATENT DOCUMENTS

| | | |
|---|---|---|
| EP | 0 211 112 A1 | 2/1987 |
| GB | 2 377 952 A | 1/2003 |
| GB | 2 431 673 A | 5/2007 |

OTHER PUBLICATIONS

International Search Report issued in PCT/US2008/081114, mailed on Mar. 5, 2009, 4 pages.
Written Opinion issued in PCT/US2008/081114, mailed on Mar. 5, 2009, 6 pages.
Official Action issued in corresponding Canadian Application No. 2,703,741; Dated Feb. 8, 2012 (2 pages).

(Continued)

*Primary Examiner* — John H Le
(74) *Attorney, Agent, or Firm* — Osha Liang LLP

(57) ABSTRACT

A system for monitoring fluids at a drilling location, the system including a viscometer (210) having a heating cup and a pump (211) in clued communication with the heating cup, wherein the pump is configured to provide a flow of fluid from a fluid line inlet to the heating cup. The system also including a cleaning fluid tank (214) including communication with the heating cup, wherein the pump is configured to provide a flow of cleaning fluid from the cleaning fluid tank to the heating cup, and a system controller (217) configured to provide instructions to the pump for controlling the flow of cleaning fluid from the cleaning fluid tanks to the heating cup.

21 Claims, 5 Drawing Sheets

OTHER PUBLICATIONS

Official Action issued in corresponding Eurasian Patent Application No. 201070530 with English language communication reporting the same; Dated May 28, 2012 (3 pages).

Official Action issued in corresponding Mexican Application No. MX/a/2010/004462 with English language communication reporting the same; Dated Aug. 28, 2012 (5 pages).

* cited by examiner

SYSTEM AND METHOD OF ANALYZING FLUIDS AT A DRILLING LOCATION

This application claims priority under 35 U.S.C. §119(e) from U.S. Provisional Application No. 60/982,805, filed on Oct. 26, 2007, which is hereby incorporated by reference in its entirety.

BACKGROUND

1. Field of the Disclosure

Embodiments disclosed herein relate generally to systems and methods for monitoring drilling at a drilling location. More specifically, embodiments disclosed herein relate to systems and methods for automated monitoring of fluids at a drilling location. More specifically still, embodiments disclosed herein relate to systems and methods for automated monitoring of fluids and for automated cleaning of fluid analyzing apparatus at a drilling location.

2. Background Art

When drilling or completing wells in earth formations, various fluids typically are used in the well for a variety of reasons. Common uses for well fluids include: lubrication and cooling of drill bit cutting surfaces while drilling generally or drilling-in (i.e., drilling in a targeted petroliferous formation), transportation of "cuttings" (pieces of formation dislodged by the cutting action of the teeth on a drill bit) to the surface, controlling formation fluid pressure to prevent blowouts, maintaining well stability, suspending solids in the well, minimizing fluid loss into and stabilizing the formation through which the well is being drilled, fracturing the formation in the vicinity of the well, displacing the fluid within the well with another fluid, cleaning the well, testing the well, transmitting hydraulic horsepower to the drill bit, fluid used for emplacing a packer, abandoning the well or preparing the well for abandonment, and otherwise treating the well or the formation.

In general, drilling fluids should be pumpable under pressure down through strings of drilling pipe, then through and around the drilling bit head deep in the earth, and then returned back to the earth surface through an annulus between the outside of the drill stem and the hole wall or casing. Beyond providing drilling lubrication and efficiency, and retarding wear, drilling fluids should suspend and transport solid particles to the surface for screening out and disposal. In addition, the fluids should be capable of suspending additive weighting agents (to increase specific gravity of the mud), generally finely ground barites (barium sulfate ore), and transport clay and other substances capable of adhering to and coating the borehole surface.

At a drilling location it is important for a drilling engineer to understand the properties of the fluids being used in the operation. Accurate fluid characterization may include understanding fluid rheology, viscosity, density and other properties of the fluids. Typically, during drilling, engineers monitor fluid properties (e.g., fluid density and gross viscosity) with tools such as mud balances and/or calibrated funnels at regular intervals (e.g., every 15 minutes or more). In certain drilling operations, fluid specialists may perform additional drilling fluid checks (i.e., mud checks) several times throughout a 24-hour period. During completion and slurry re-injection operations, engineers may perform similar tests on fluids to determine the properties of the fluids. Such fluid tests may thereby allow engineers to adjust fluid parameters to optimize drilling conditions.

Accordingly, there exists a continuing need for methods and systems of monitoring fluids at a drilling location.

SUMMARY OF THE DISCLOSURE

In one aspect, embodiments disclosed herein relate to a system for monitoring fluids at a drilling location including a viscometer having a heating cup and a pump in clued communication with the heating cup, wherein the pump is configured to provide a flow of fluid from a fluid line inlet to the heating cup. The system also including a cleaning fluid tank including communication with the heating cup, wherein the pump is configured to provide a flow of cleaning fluid from the cleaning fluid tank to the heating cup, and a system controller configured to provide instructions to the pump for controlling the flow of cleaning fluid from the cleaning fluid tanks to the heating cup.

In another aspect, embodiments disclosed herein include a method for automated fluid monitoring at a drilling location, the method including providing automation controller for a fluid analyzer for controlling the automated fluid monitoring. The controls including instructions for introducing a fluid into a fluid analyzer, the fluid analyzer including a viscometer having a heating cup. Additionally, the controls including instructions for analyzing the fluid with the fluid analyzer, wherein the analyzing includes determining fluid properties, removing the fluid from the fluid analyzer, introducing a cleaning fluid into the heating cup, executing a cleaning operation, and draining the cleaning fluid from the heating cup.

In another aspect, embodiments disclosed herein include a method for automated fluid analyzer cleaning at a drilling location, the method including introducing a cleaning fluid into the fluid analyzer and actuating the fluid analyzer. Additionally, the method including draining the cleaning fluid from the fluid analyzer, wherein the introducing, actuating, and draining are controller through automation instructions provided by a system controller.

Other aspects and advantages of the invention will be apparent from the following description and the appended claims.

DETAILED DESCRIPTION

Figure 1:
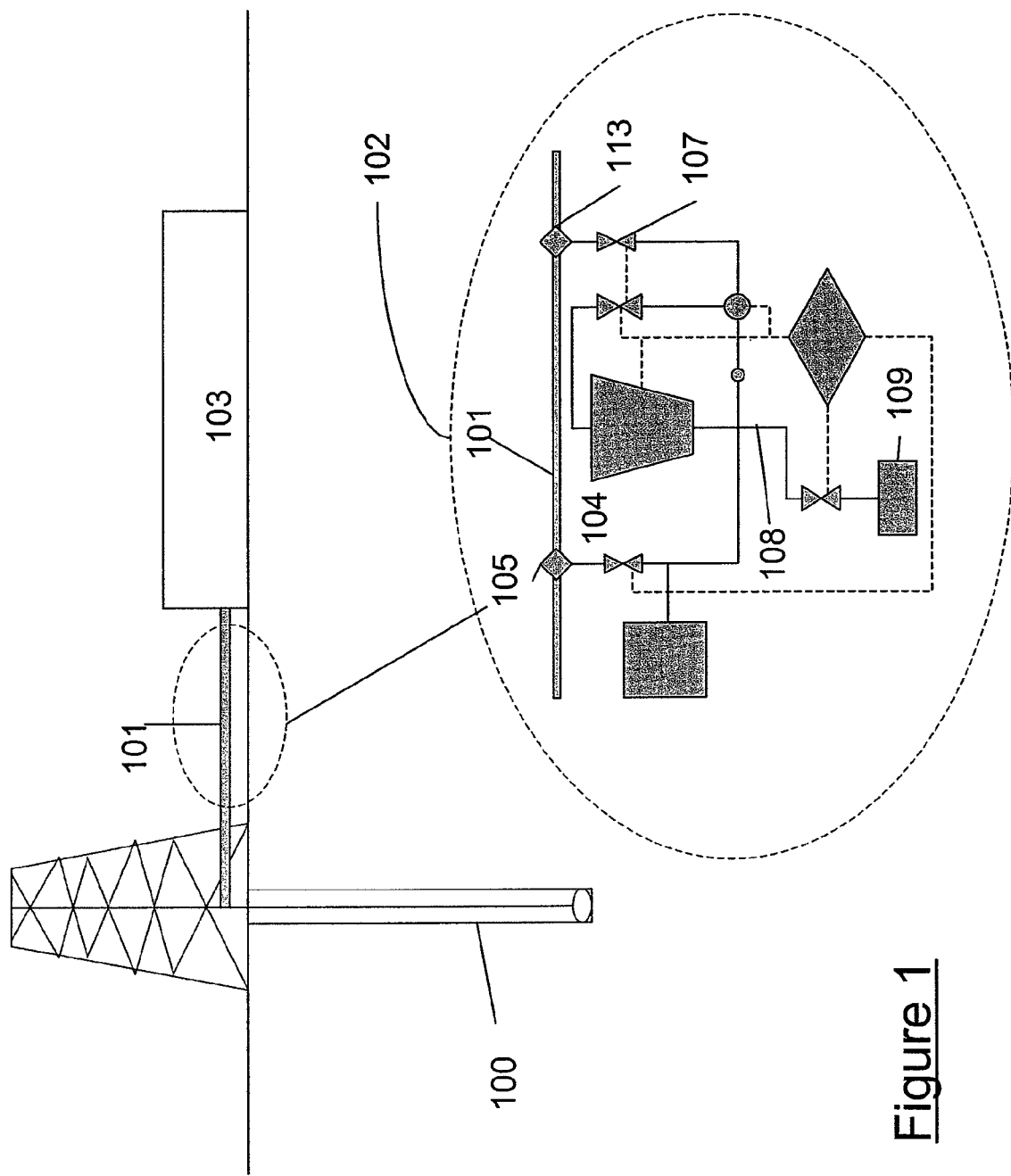
FIG. 1 is a schematic representation of a system for monitoring fluids at a drilling location according to one embodiment of the present disclosure.

Embodiments disclosed herein relate generally to systems and methods for monitoring drilling at a drilling location. More specifically, embodiments disclosed herein relate to systems and methods for automated monitoring of fluids at a drilling location. More specifically still, embodiments disclosed herein relate to systems and methods for automated monitoring of fluids and for automated cleaning of fluid analyzing apparatus at a drilling location.

As a well is drilled, drilling fluid is pumped downhole to, among other things, facilitate drilling, cool and lubricate the drill bit, and remove solid particles from the wellbore. As the drilling fluid circulates through the wellbore, solid particles, including drill cuttings, become entrained within the drilling fluid and are conveyed from the wellbore to the surface of the drilling operation. Because characteristics of the drilling fluid may change as a result of the circulation of the fluid through the wellbore, those of ordinary skill in the art will appreciate that monitoring of the drilling fluid may be beneficial. Examples of fluid characteristics that may change include fluid density, viscosity, rheology, temperature, and pH, as well as components of the drilling fluid. Also, as the drilling fluid circulates through the wellbore, the fluid removes entrained cuttings, and as such, characteristics of the drilling fluid may be affected by the addition of drill cuttings, hydrocarbons, and other contaminants.

In addition to drilling fluid including entrained cuttings removed during drilling, the drilling fluid may also contain substances added to the fluid to produce desired drilling conditions. Exemplary drilling fluid additives may include pH control additives, corrosion inhibitors, defoamers, emulsifiers, filtrate reducers, flocculants, foaming agents, hydrate suppressants, lost circulation materials, lubricants, temperature stability agents, dispersants, viscosifiers, and weighting agents. Control of the levels of these additives may be important in maintaining optimal drilling parameters, including drilling fluid formulation, to produce optimized drilling conditions. Those of ordinary skill in the art will appreciate that improperly formulated drilling fluids may results in inefficient drilling, damaged wellbores, and environmental contamination. Additionally, those of skill in the art will appreciate that the timely modification of drilling fluid parameters during drilling may enhance drilling conditions so as to, for example, increase drilling rate of penetration, increase drilling efficiency, and increase environmental remediation of drilling waste, etc.

While fluids are used in drilling, fluids are also used during other aspects of operations at drilling locations. For example, fluids may also be used during well completion, workover operations, and in the form of slurries during cuttings re-injection. These alternate operations may also benefit from fluid monitoring, as well as the determination of specific fluid properties, such as, for example, completion fluid and/or slurry viscosity and rheology. Monitoring of such fluid properties may further allow for the optimization of completion, well workover, and cuttings re-injection at a drilling location.

Referring to FIG. 1, a schematic representation of a system for monitoring fluids at a drilling location is shown. In this embodiment, a drilling engineer collects drilling fluid from a wellbore 100 during the drilling of a well. The collection process may include diverting a return flow 101 of drilling fluid from wellbore 100 to a fluid monitoring system 102 prior to processing of the drilling fluid being processed by cleaning equipment 103 (e.g., vibratory shakers, degassers, centrifuges, hydrocyclones, etc.).

As drilling fluid returns from wellbore 100, the fluid flows through return line 101. When a drilling engineer determines that properties of the fluid should be monitored, the drilling engineer may actuate an inlet valve 104 in fluid communication with an inlet 105 of return line 101. Tests on the fluid may then be performed by fluid monitoring system 102, as will be described in detail below. After the tests are completed, an outlet valve 107 may be opened, and the fluid may then be pumped through an outlet 113 of return line 101.

The tested fluid may then re-enter return line 101 and be pumped to downstream cleaning equipment 103. In alternate embodiments, tested fluids may be discharged from fluid monitoring system 102 via a discharge line 108 and into a discharge tank 109. Such a discharge process may be beneficial in a fluid monitoring system 102 that includes the use of chemicals that may damage the fluid, cleaning equipment 103, or other aspects of the drilling operations. However, those of ordinary skill in the art will appreciate that generally, the fluids may be reintroduced into an active fluid system of the drilling operation or cleaning and reuse.

While not described in detail, those of ordinary skill in the art will further appreciate that other fluids may be monitored at a drilling location in accordance with embodiments of fluid monitoring system 102 disclosed herein. For example, during completion, completion fluids may enter and exit fluid monitoring system 102 as described above. Additionally, during cuttings re-injection operations, fluid monitoring system 102 may be configured to receive a flow of cuttings slurry prior to injection into wellbore 100. In such an embodiment, fluid monitoring system 102 would receive a flow of cuttings slurry from a cuttings re-injection system (not shown) instead of from return line 101, such that properties of the slurry could be monitored and adjusted prior to injection into wellbore 100. Those of ordinary skill in the art will appreciate that other fluids used at drilling locations not specifically discussed herein may also benefit from embodiments of the present disclosure.

Figure 2:
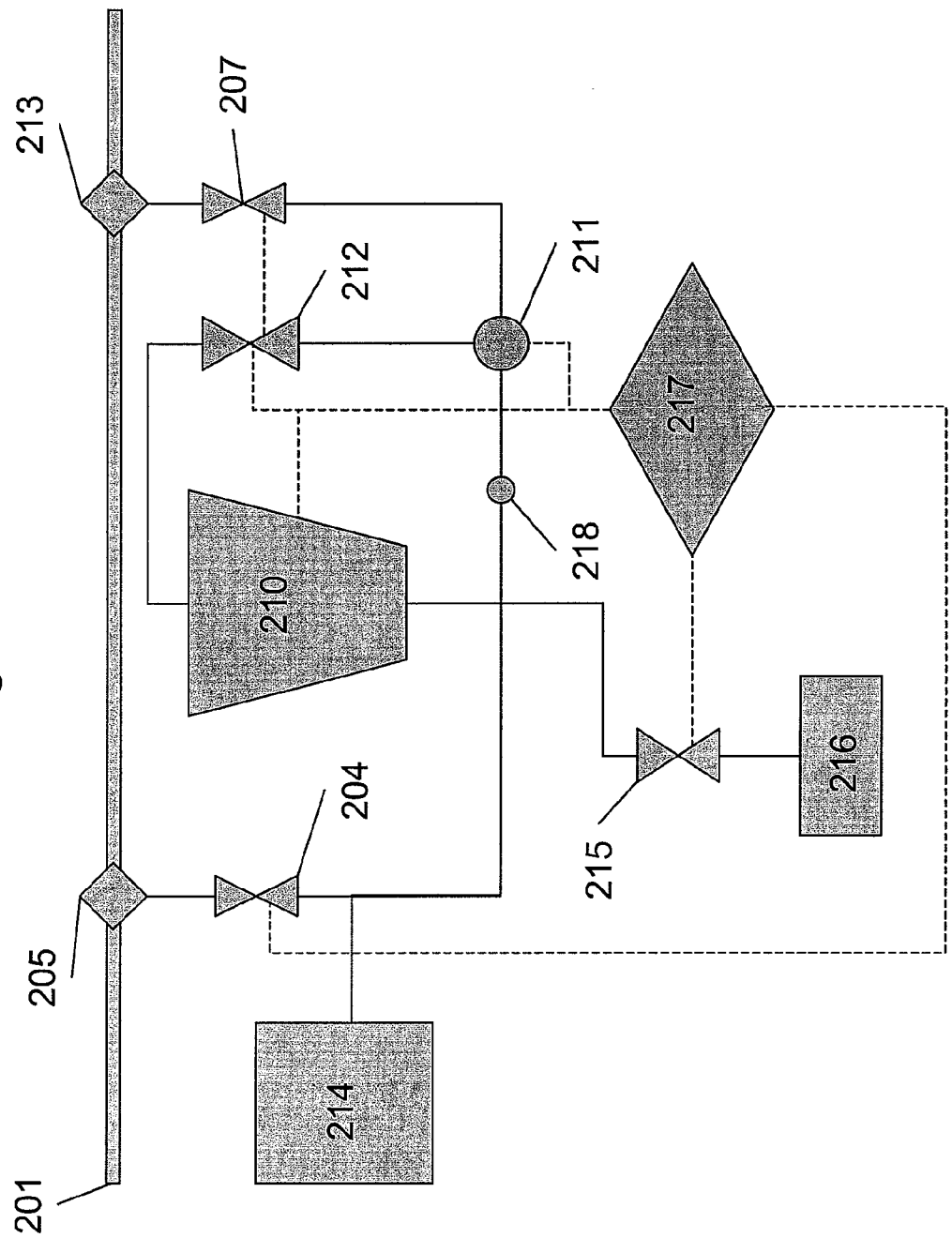
FIG. 2 is a schematic representation of a system for monitoring fluids according to one embodiment of the present disclosure.

Referring to FIG. 2, a blowup of a fluid monitoring system according to embodiments of the present disclosure is shown. In this embodiment, fluid returns from a wellbore through return line 201. Generally, the fluid is allowed to circulate through the active drilling system, thereby bypassing fluid test apparatus. However, when a drilling operation wishes to run a test or otherwise monitor the fluid, inlet valve 204 may be opened, such that a flow of fluid enters the fluid monitoring system through an inlet 205.

To provide for the introduction of the fluid into a viscometer 210 at to a predetermined volume and at a correct flow rate, a pump 211 is actuated, and a control valve 212 is opened to allow a flow of fluid from inlet 205 to viscometer 210. In this embodiment, pump 211 is a pneumatic pump, however, those of ordinary skill in the art will appreciate that in alternate embodiments, pump 211 may be any type of pump capable of providing a flow of fluid through a test apparatus. In other embodiments, pump 211 may include, for example, any type of positive displacement pump, centrifugal pump, diaphragm pump, or kinetic pump. Those of ordinary skill in the art will appreciate that in certain embodiments, pump 211 may not be necessary to supply a flow of fluid to viscometer 210. In such an embodiment if the pressure in the return line is sufficient to drive the fluid into viscometer, pump 211 may either be excluded from the system, or otherwise not used.

To ensure proper line pressures, a pressure gauge 218 is disposed between fluid inlet 205 and pump 211. Pressure gauge 218 allows a drilling operator to monitor pressure in the fluid line to determine if the fluid pressure is within operational limits. As such, pressure gauge 218 may allow the fluid monitoring system or the operator to stop the flow of fluid should a pressure fall outside of the operational limits, thereby protecting the system from adverse well conditions.

When a drilling engineer begins a fluid test, pump 211 is actuated and a predetermined volume of fluid is pumped into viscometer 210. When the predetermined volume of fluid for the test is in viscometer 210, control valve 212 is closed and an outlet valve 207 is opened to allow residual fluid to exit the fluid monitoring system. As residual fluid is removed from the fluid monitoring system, inlet valve 204 may be closed such that no additional fluid enters the fluid monitoring systems. In certain embodiments, it may be beneficial to allow both inlet valve 204 and outlet valve 207 to remain open, thereby allowing a flow of drilling fluid through the fluid monitoring system. However, in other embodiments, after the fluid is injected into viscometer 210, inlet valve 204 is closed, such that the return flow of drilling fluid remains in return line 201. In such an embodiment, the pressure in the system is not affected by the pressure of the return flow of drilling fluid in return line 201.

After the fluid is tested in viscometer 210, pump 211 is actuated to remove the fluid from viscometer 210. During fluid removal, outlet valve 207 is opened to allow the fluid to be pumped back through an outlet 213 into return line 201 and back into the active system. In other embodiments, fluid may be removed from viscometer 210 and discarded, such that tested fluid does not re-enter the active system. Such an embodiment may be beneficial if chemicals are used in the testing, or if conditions of the test alter the fluid so that it could damage components of the active fluid system.

When the fluid is removed from viscometer 210, the drilling engineer may begin a cleaning operation. During a cleaning operation, cleaning fluid is pumped from a cleaning fluid tank 214 via pump 211 through open control valve 212 and into viscometer 210. The cleaning fluid may include water, base oil, surfactants, and other substances that may remove residual drilling fluid from internal components of viscometer 210. Cleaning fluid tank 214 may also include components to monitor, for example, cleaning fluid levels, pressure within the cleaning fluid tank 214, and flow rates of cleaning fluid out of cleaning fluid tank 214. In alternate embodiments, one or more valves may be disposed between cleaning fluid tank 214 and pump 211 to further control the flow of cleaning fluid therethrough.

During the cleaning operation, viscometer 210 may be actuated such that a bob (not shown) or a sleeve (not shown) of the viscometer is rotated, thereby stirring the cleaning fluid in viscometer 210. The movement inside viscometer 210 along with the cleaning fluid may dissolve solid particles and substances that may become adhered to the internal components of viscometer 210 during the test. Those of ordinary skill in the art will appreciate that cleaning operations, and movement of internal components of viscometer 210 may last for several minutes (e.g., 5 minutes) or until the internal components of viscometer 210 are substantially clean.

After the cleaning cycle is complete, the cleaning fluid may be drained from viscometer 210 via opening a discharge valve 215 providing fluid communication between viscometer 210 and a discharge tank 216. In this embodiment, providing a flow of used cleaning fluid to discharge tank 216 may thereby prevent cleaning fluids from entering the active fluid system. In alternate embodiments, the cleaning fluid may be discharged into the active fluid system if the cleaning fluid being used is benign with respect to components of the drilling system, or with respect to the fluids being used in the drilling operation. In still other embodiments, cleaning fluid may be recycled back into cleaning fluid tanks 214 for reuse in further cleaning operations. Such an embodiment may be useful when the fluid being tested does not readily adhere to the internal components of viscometer 210, or when the fluid may be separated from cleaning fluid in cleaning fluid tanks 214. To facilitate the separation of recycled cleaning fluid from fluid that may accumulate in cleaning fluid tank 214, skimmers (not shown) or other removal apparatus, such as level valves (not shown) may also be used to provide for active removal or siphoning of separated fluids from cleaning fluid tanks 214. Those of ordinary skill in the art will appreciate that cleaning fluid tanks 214 components such as level sensors (not shown) may further provide for monitoring of fluid levels within the tank.

Upon removal of the cleaning fluid from the fluid monitoring system, the system is in condition for a second fluid test. As such, inlet valve 204 may be opened, and fluid from return line 201 may be pumped via pump 211 through open valve 212 and into viscometer 210. Those of ordinary skill in the art will appreciate that the testing and cleaning cycles may be repeated so that monitoring of fluids in the active fluid system may be automatically monitored. Additionally, in certain embodiments the automated control of the fluid tests and cleaning operations may occur without drilling operator input. However, in certain aspects, and at certain times during a drilling operation, a drilling engineer may request either a test or a cleaning operation be run. As such, embodiments of the present disclosure provide for a manual override to the system, thereby giving the drilling engineer control over the fluid monitoring system. Such demand based test and cleaning cycles are discussed in detail below.

The automated control of the fluid monitoring system may be through instructions provided by a system controller 217. System controller 217 may include a programmable logic controller ("PLC"), a personal computer, or other means of providing instructions to the fluid monitoring system as would be known to those of ordinary skill in the art. In this embodiment, system controller 217 is functionally connected to inlet, control, discharge, and outlet valves 204, 207, 215, and 212 respectfully, viscometer 210, cleaning fluid tanks 214, and pump 211, as is illustrated by the dashed lines of FIG. 2. Functional control may include direct connections, such as wiring, or remote connection, such as may be provided by intranet or internet protocols transmitted wirelessly.

System controller 217 is generally configured to provide instructions to components of fluid monitoring system for controlling the transfer of fluids throughout the system, as well as monitoring and outputting results of the fluid tests and cleaning operations. For example, system controller 217 provides instructions for actuating pump 211 and components of cleaning fluid tank 214 to provide a flow of cleaning fluid between cleaning fluid tank 214 and viscometer 210. Additionally, system controller 217 provides instructions for monitoring viscometer 210, the pressures within the fluid monitoring system via pressure gauge 218, and the output of test results from viscometer 210. In certain embodiments, system controller 217 may include a network of system controllers, such that multiple PLCs are employed to control different aspects of the fluid monitoring system. In such an embodiment, a first PLC may be configured to monitor the test, a second PLC may be configured to monitor the cleaning operation, and a third PLC may be configured to transmit results of the test to an output device (e.g., a monitor, a printer, or a network). In still other embodiments, both PLCs and computer systems may be used for different aspects of the operation. Those of ordinary skill in the art will appreciate that varied configurations of system controllers 217 are within the scope of the present disclosure, and as such, the configuration of system controllers 217 within the fluid monitoring system is not a limitation of the present disclosure.

Figure 3:
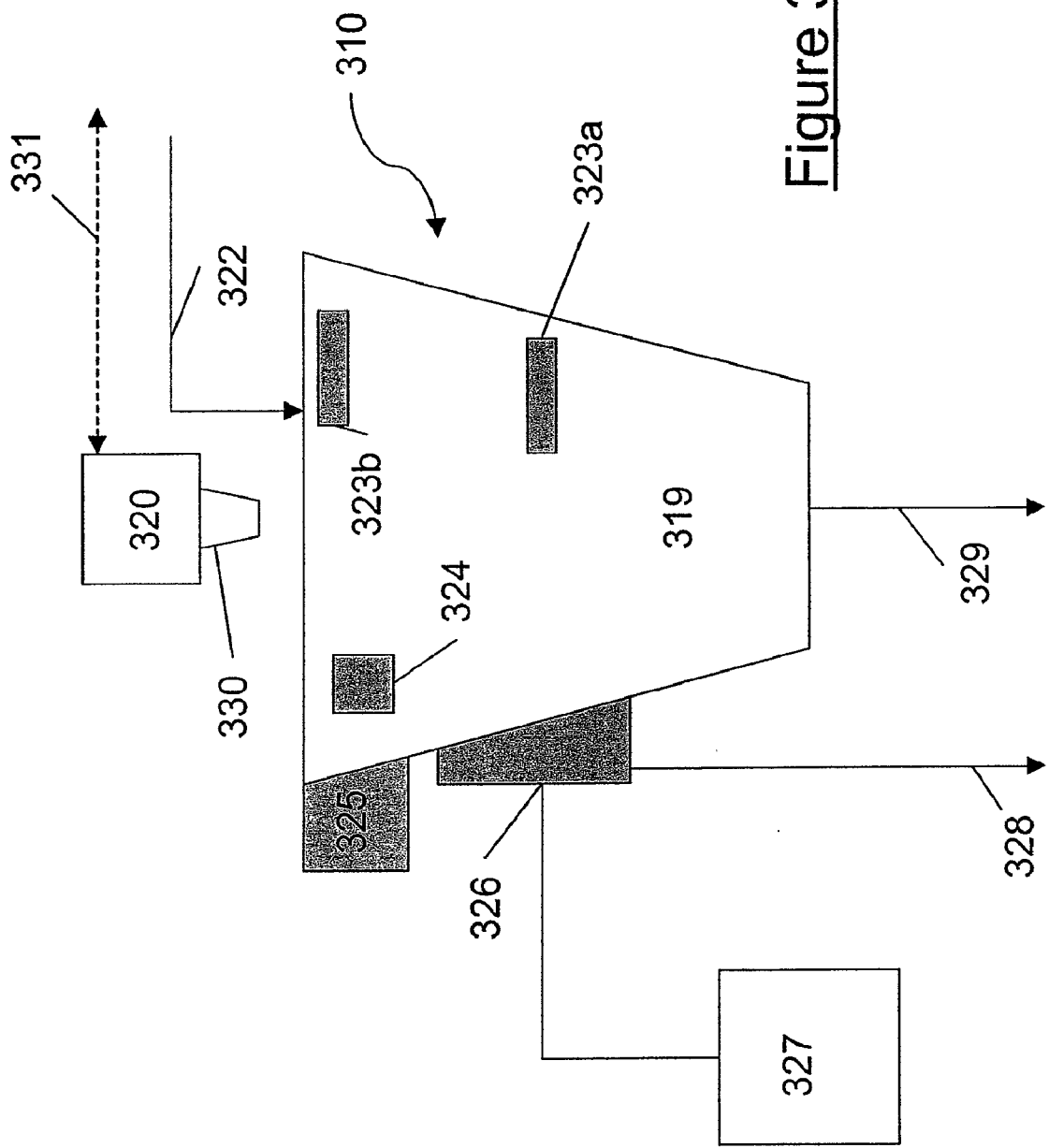
FIG. 3 is a schematic representation of a system for monitoring fluids according to one embodiment of the present disclosure.

Referring to FIG. 3, a schematic representation of a system for monitoring fluids according to one embodiment of the present disclosure is shown. In this embodiment, a viscometer 310 and components of the fluid monitoring system used to test, and in certain aspects clean viscometer 310, are discussed in detail. As illustrated, viscometer 310 includes a heating cup 319 and a viscometer head 320. Heating cup 219 is a low volume vessel configured to receive a flow of fluids from the active drilling system, as described above. The flow of fluids may be pumped into heating cup 319 via a heating cup inlet 322, which provides fluid communication between heating cup 219 and a pump (not shown). Additionally, heating cup inlet 322 provides fluid communication between heating cup 319 and a cleaning fluid tank (not shown) and other components of the fluid monitoring system. In this embodiment, heating cup 319 may include a vessel capable of receiving 500 ml of fluid; however, in alternate embodiments, different volume heating cups 319 may be used according to the requirements of the specific tests being performed.

To monitor the volume of fluid injected into heating cup 319, a plurality of fluid level sensors 323 may be disposed in or around heating cup 319. A base fluid level sensor 323a may provide a base level, otherwise recognized as the minimum volume of fluid required to perform a test. A secondary level sensor 323b may provide a second level indicating a maximum allowable fluid level in heating cup 319 for a test to be performed. In certain embodiments, secondary level sensor 323b may also serve as a redundant overflow sensor, thereby informing a drilling engineer or a system controller when an overflow condition exists. Those of ordinary skill in the art will appreciate that in certain embodiments, additional sensors capable of indicating a fluid level within heating cup 319 may be used, so as to replace the dual function of secondary level sensor 323b, or to otherwise provide additional information regarding the volume of fluid within heating cup 319. Additionally, level sensors 323 may provide information to the system controller to indicate a level of cleaning fluid within heating cup 319.

In addition to level sensors 323, one or more temperature controllers 324 may be functionally disposed in or on heating cup 319. Temperature controllers 324 may provide data to system controller indicating the temperature of heating cup 319, fluids within heating cup 319, or of other components of the fluid monitoring system. To provide heat to heating cup 319, a heating element 325 is disposed around heating cup 319. Heating element 325 provides a source of heat to heating cup, such that the temperature of fluids within heating cup 319 may be increase to optimal test levels. Generally, temperatures used during fluid testing may range between 25° C. and 50° C.; however, in certain embodiments, depending on the specific tests being performed, heating element 325 may preferably be capable of heating the fluids to approximately 80° C. Those of ordinary skill will appreciate that the temperature ranges discussed above are exemplary in nature. In certain embodiments, fluids may be tested at temperatures of less than 25° C. or greater than 80° C.

After the temperature of the fluids and/or heating cup 319 is increased with heating element 325, the temperature may need to be decreased prior to performing cleaning operations. To speed the cooling of the fluids and components of the system, a cooling jacket 326 may be disposed around heating cup 319. In this embodiment, cooling jack 326 is in fluid communication with a cold-water tank 327, such that cold water may be pumped into cooling jacket 326 to speed the cooling of heating cup 319 and the fluids contained therein. After cooling jacket 326 uses the cold water, the water may be discarded to a waste water drain 328. In other embodiment, the cold water may be recycled from cooling jacket 326 back into cold-water tank 327.

As described above, after a fluid test or a cleaning operation is performed, waste fluids and cleaning fluids are removed from heating cup 319 via a discharge port 329. In this embodiment, discharge port 329 is located at the bottom of heating cup 319 such that gravity may primarily provide for the removal of the fluids. However, in alternate embodiments, discharge port 329 may be located at a different location on heating cup 319, and additional components may be used to facilitate the removal of fluids from heating cup 319. Additional components may include pumps, siphoning devices, or vacuums, and may further eliminate residual fluids in heating cup 319.

The fluid monitoring system also includes a viscometer head 320 configured for use with heating cup 319. In this embodiment, viscometer head 320 includes a bob 330 configured to rotate within heating cup 319 such that fluid properties may be determined. In other aspects of the present disclosure, other types of viscometers known in the art including, for example, viscometers having rotable sleeves, may be used according to embodiments disclosed herein. Viscometer 310, including viscometer head 310 and the components of viscometer 310 and heating cup 319 discussed above, may be controlled via a system controller. The system controller is functionally connected to viscometer 310, as illustrated by dashed line at 331. Those of ordinary skill in the art will appreciate that additional components may be included in alternate configurations of the present disclosure. Such additional components may include, for example, temperature probes, temperature sensors, viscometer temperature probes, pH monitors, redundant overflow sensors, additional valves, pressure sensors, check valves, isolation valves, or other components as may be required to provide optimal fluid testing and equipment cleaning operations.

Figure 4:
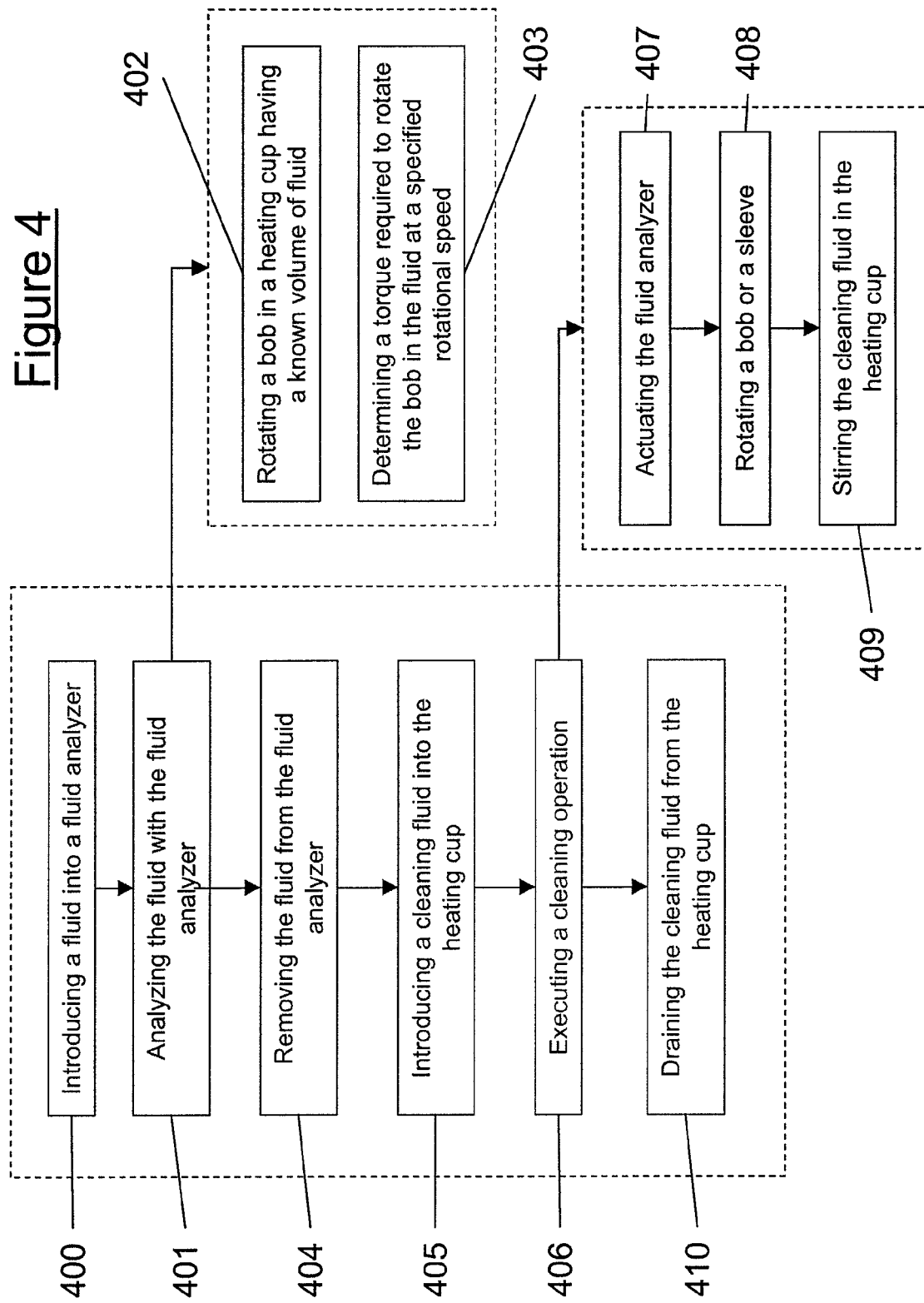
FIG. 4 is a flowchart of a method for monitoring fluids according to one embodiment of the present disclosure.

Referring to FIG. 4, a flowchart of a method of monitoring fluid properties according to an embodiment of the present disclosure is shown. In this embodiment, a fluid is introduced (400) into a fluid analyzer. The fluid analyzer may include a viscometer or other device capable of determining, for example, fluid viscosity and rheological properties. Introduction (400) of the fluid may also include the methods described above. In one aspect, a specific volume of fluid, for example, 300 ml may be introduced (400) by pumping the fluid from a return line at a drilling location into the fluid analyzer.

After introducing (400) the fluid, the fluid is analyzed (401) with the fluid analyzer. The analyzing (401) may include rotating (402) a bob or sleeve of fluid analyzer with respect to a heating cup of the fluid analyzer, such that a torque required to rotate the bob through the fluid at a specified rotational speed is determined (403). The determined (403) torque may then be used to calculate a viscosity and the rheological properties of the fluid. The determined (403) viscosity and/or rheological properties of the fluid may then be output for further processing or storing as will be described in detail below.

Upon completion of the fluid test, the fluid is removed (404) from the fluid analyzer, and a cleaning fluid is introduced (405) into the heating cup. A specified volume of fluid may be introduced (405), such that upon actuation of the viscometer during a cleaning operation, the fluid contacts at least the bob and internal walls of the heating cup to facilitate the removal of residual fluids therefrom. Those of ordinary skill in the art will appreciate that the volume of cleaning fluid introduced (405) into heating cup may vary according to the properties of the fluid being tested, but generally should be at least a similar volume as used during the initial fluid test.

After introducing (405) cleaning fluid into the heating cup, a cleaning operation is executed (406). The cleaning operation includes actuating (407) the fluid analyzer such that the bob or sleeve of the fluid analyzer is rotated (408) with respect to the heating cup. Generally, the rotation (408) of the relative component parts of the fluid analyzer will cause the cleaning fluid to be stirred (409), such that the cleaning fluid contacts the bob and/or sleeve, as well as the internal walls of the heating cup. Those of ordinary skill in the art will appreciate that the rotational speed used will vary according to the properties of the tested fluid; however, in certain embodiments, the bob/sleeve should be rotated for at least 5 minutes at 300 rotations per minute. In certain embodiments, if a particularly thick or solid laden fluid is being tested, a longer cleaning operation may be required to properly clean the components of the fluid analyzer. Likewise, if particularly thin fluids are being tested, shorter cleaning operations may be used.

When the cleaning operation is complete, the cleaning fluid is drained (410) from the heating cup, and the fluid analyzer is in condition for another test cycle. In certain embodiments, multiple cleaning operations may be used to further clean components of the fluid analyzer. For example, in an embodiment wherein a particularly thick fluid is being tested, a system controller may determine, based on readings from fluid analyzer sensors, that residual fluid or solids remain in the heating cup or on the bob/sleeve after the cleaning operation. The system controller may then delay a test cycle, and instead run a second cleaning operation. Alternatively, the system controller may run the test cycle, but inform a drilling engineer that the fluid analyzer is not operating in optimal condition. In still other embodiments, the fluid analyzer may stop the test cycle from running and inform the drilling engineer that the fluid analyzer needs to be inspected. Those of ordinary skill in the art will appreciate that the system controller may therein verify the operating condition of the fluid analyzer and components of the fluid monitoring system so as to ensure optimal operating conditions are maintained.

Additionally, because the testing and cleaning operations of the fluid monitoring system may be substantially automated, the drilling engineer may not be required to constantly monitor the fluid analyzer. For example, in the embodiment described above, the system controller may provide instructions to the fluid analyzer and components of the fluid monitoring system to automate both the test cycle and the cleaning operation. Because the system controller does not require a drilling engineer to manually adjust the fluid analyzer (e.g., add fluids or cleaning the components) between tests, the fluid monitoring system may function without substantial human input.

Figure 5:
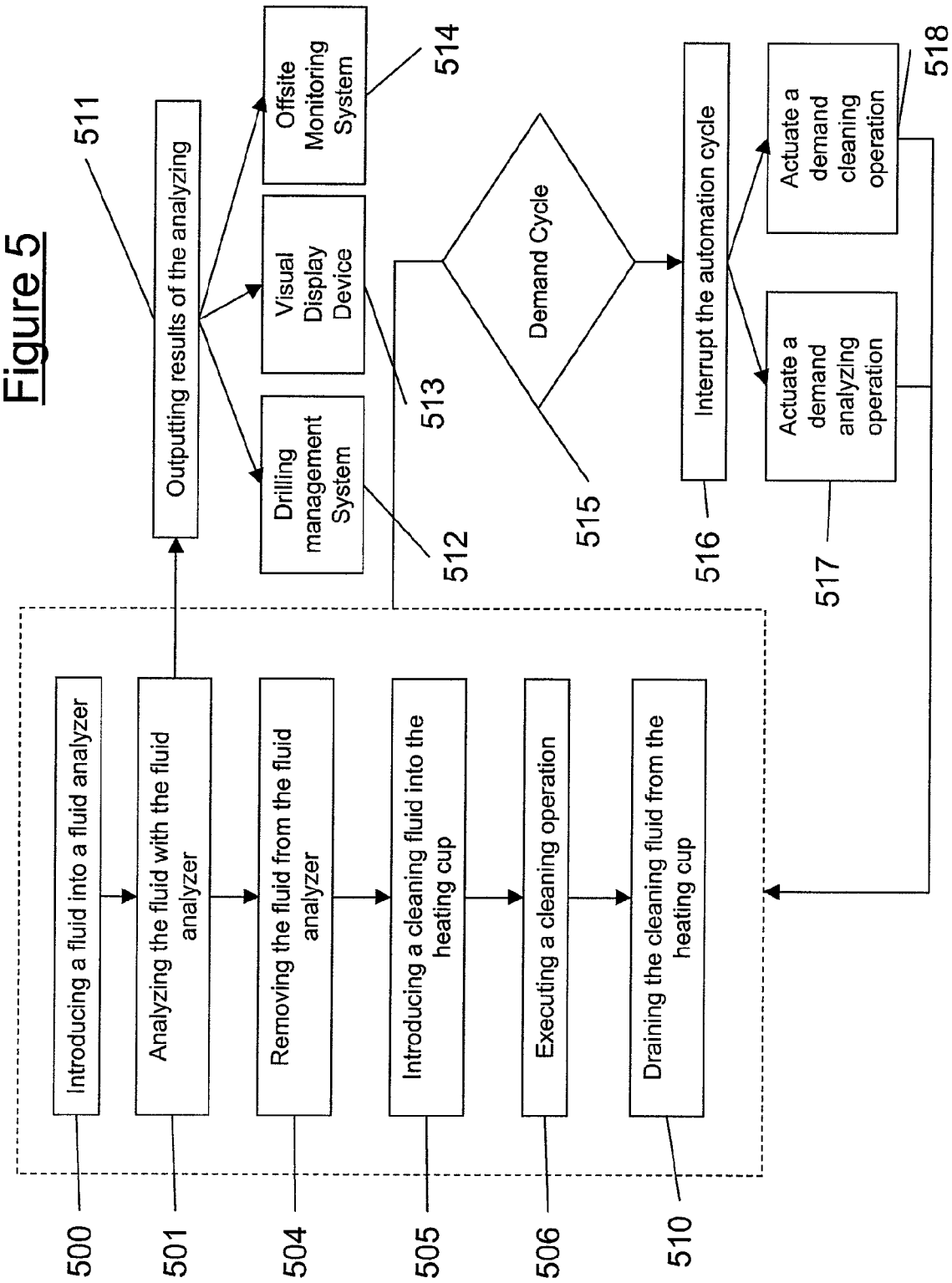
FIG. 5 is a flowchart of a method for monitoring fluids according to one embodiment of the present disclosure.

To further explain the operational logic of the fluid monitoring system, now refer to FIG. 5, wherein a flowchart of a system for monitoring fluids in accordance with an embodiment of the present disclosure is shown. In this embodiment, the process as described in FIG. 4 with respect to steps 400 through 410 is substantially similar to the steps 500, 501, 504, 505, 506, and 510 of FIG. 5. Generally, a fluid is introduced (500) into a fluid analyzer, analyzed (501) with the fluid analyzer, and removed (504) from the fluid analyzer. Subsequently, a cleaning fluid is introduced (505) into a heating cup, a cleaning operation is executed (506), and the cleaning fluid is drained (510) from the heating cup. The above-described steps describe the primary function of the fluid analyzer during the testing and cleaning operations.

In certain embodiments, additional functions may be performed by the fluid monitoring system contemporaneous to the above described steps. For example, in this embodiment, after the fluid is analyzed (501) with the fluid analyzer, the results of the test are output (511) from the fluid analyzer to one or more of a drilling management system (512), a visual display device (513) and/or an offsite monitoring system (514). The output (511) function may include transferring test data from the fluid analyzer to a system controller for additional analysis, or alternatively, the fluid analyzer may analyze the data, and only the results of the test may be transferred to the system controller. In still other embodiments, the test data or results may be directly sent to the drilling management system (512), the visual display device (513), or the offsite monitoring system (514).

In this embodiment, the drilling management system (512) may include programs or systems used on drilling rigs for monitoring and controlling drilling parameters. Drilling parameters that may be monitored and/or controlled by the drilling management system (512) include drilling fluid flow rate, torque on bit, rotational speed of a drill bit, and other properties as would be known to those of ordinary skill in the art. By providing the drilling management system (512) with fluid properties, such as viscosity and rheology, the drilling management system (512) or engineers in control thereof may be able to adjust drilling parameters to compensate for drilling fluid parameters. Alternatively, the system controller of the present application may use data from the drilling management system (512) to adjust drilling fluid parameters in view of the drilling parameters used by the drilling management system (512).

Results output (511) to a visual display device may include outputting (511) test data and/or results data to a monitor, or other device capable of displaying the data. Additionally, the data may be displayed as both graphical and numerical representations including, for example, graphs of fluid viscosity, data-tables of viscosities, and cumulative data collected over time. In certain embodiments, the visual display device may also include input functionality, such as input peripherals or a touch screen, such that a drilling engineer may adjust parameters of the test or cleaning operation directly from the display device.

Offsite monitoring system (514) may include labs and monitoring facilities located away from the drilling location. An exemplary lab may include a fluid analysis lab, wherein a drilling engineer may use information output (511) by the fluid analyzer to determine adjustments for fluid parameters (e.g., viscosity, density, and composition). As such, offsite monitory systems (514) in communication with embodiments of the present disclosure by, for example, networks, may provide for the transfer of drilling fluid information between onsite and offsite locations.

In addition to embodiments of the present disclosure providing means for outputting (511) data from the fluid monitoring system, the test and cleaning cycles of the present system may be executed according to varied sequencing. For example, in certain embodiments, a drilling engineer may indicate that the fluid monitoring system should automatically perform intermittent tests. In such an embodiment, the drilling engineer may program the system controller of the fluid monitoring system to perform a fluid analysis according to a time profile (e.g., every 5, 10, or 15 minutes). However, in other embodiments, a drilling engineer may interrupt an automated sequence with specific instructions to perform a test. Similarly, a drilling engineer may program the fluid monitoring system with cleaning operation execution instructions to perform one or more cleaning operations between test cycles.

Referring back to FIG. 5, an exemplary demand cycle (515) interrupting an automated cycle is illustrated in detail. In this embodiment, demand cycle (515) includes a drilling operator interrupting (516) the automated testing sequence. As illustrated, interrupting (516) the automated testing includes actuation (517) of a demand analyzing operation or actuation (518) of a demand cleaning operation. A demand analyzing operation includes running a test with the fluid analyzer and the processes necessary to complete such test. Similarly, a demand cleaning operation includes introducing a cleaning fluid into the fluid analyzer, executing a cleaning operation, and any additional steps necessary to clean the fluid analyzer.

In certain embodiments, both testing and cleaning cycles may be automated. In such embodiments, a system controller may provide automation controls for the fluid analyzer for controlling the automated fluid monitoring system. These instructions, as explained in detail above, include directions to both test a fluid and clean the fluid analyzer after the tests. In other embodiments, instructions for controlling the operation of the fluid monitoring system may be downloaded to the fluid analyzer from an offsite location. Such instructions may include protocols for a demand analysis or demand cleaning operation.

In operations including offsite monitoring, or onsite monitoring that is located in another building at the drilling location, the fluid monitoring system may include cameras for direct monitoring of the analysis and/or testing. Exemplary cameras may include digital still cameras, digital video cameras, closed-circuit cameras, or other types of cameras known to those of ordinary skill in the art. In certain embodiments, such cameras may be configured to interface directly with a system controller of the fluid monitoring system, such that a drilling engineer at an offsite location may control aspects of the analysis and cleaning operations remotely. Those of ordinary skill in the art will appreciate that embodiments that do not include a camera system may also be remotely controlled from an offsite location by providing instructions to the system controller in response to, for example, specific output results provided by the fluid monitoring system.

Advantageously, embodiments of the present disclosure for the monitoring of drilling fluid rheology at a drilling location. Because a drilling engineer does not have to manually test the drilling fluid, a time consuming and potentially dangerous process, the drilling fluid properties may be tested more frequently. More frequent drilling fluid tests may allow for intermittent alterations to the drilling fluid to optimize the fluid for the specific conditions of the wellbore being drilled. Additionally, the automated process of monitoring fluid rheology may provide drilling engineers with a substantially continuous update of the condition of the fluid in the wellbore. Such continuous monitoring may allow for quicker adjustments to the drilling fluid and/or drilling parameters, such that drilling may be more efficient.

Also advantageously, embodiments of the present disclosure may be used with multiple types of fluids used at drilling locations. In certain embodiments, completion fluids may be monitored during well completion operations. By measuring fluid properties of completion fluids, damage to the wellbore and completion tools, such as production liners, packers, downhole valves, and shooting perforators may be avoided. Additionally, a determination of completion fluid viscosity during a completion operation may inform a drilling operator when solids content in a near-wellbore area has reached levels that may interfere with either the well completion or later production operations.

Embodiments of the present disclosure may also be advantageously used in the re-injection of cuttings into a wellbore. In such an embodiment, the fluid properties of a re-injection slurry may be monitored prior to injection to ensure a proper slurry viscosity. Because the viscosity may be monitored with greater frequency during cuttings re-injection, a proper concentration of solids content within the slurry may be determined. By determining a proper solids content for the specific re-injection, problems associated with slurries having too great a solids content, such as the accidental release of injected slurry into the environment, excessive erosion wear from injection, and well plugging in the instance of improper slurry rheology, may be avoided. By decreasing the risks associated with cuttings re-injection, zero discharge operations, which are beneficial to the environment, may be achieved. Additionally, because cuttings re-injection may be less expensive than land disposal, the slurry monitoring processes disclosed herein may decrease the risks associated with a less expensive process for disposing drilling waste.

Advantageously, embodiments disclosed herein provide a self-cleaning system for monitoring of fluid rheology at a drilling location. Because embodiments of the present disclosure are self-cleaning during normal operations, the fluid monitor may continue to provide accurate test results after multiple tests. Moreover, embodiments disclosed herein may provide for the remote control of the monitoring operations, such that a drilling engineer located offsite may be able to control and receive data from the fluid monitor. Remote access to control of the fluid monitor may further allow drilling engineers to monitor fluids, order a fluid test at a specific time, and monitor operating conditions of the fluid monitor. Remote access, control, and command over test and cleaning operations may thereby result in the substantially continuous monitoring of fluids at a drilling location. Such monitoring practices may thereby allow for adjustments to fluid parameter and more efficient fluid operation within the wellbore.

While the present disclosure has been described with respect to a limited number of embodiments, those skilled in the art, having benefit of this disclosure, will appreciate that other embodiments may be devised which do not depart from the scope of the disclosure as described herein. Accordingly, the scope of the disclosure should be limited only by the attached claims.

What is claimed is:

1. A system for monitoring fluids at a drilling location comprising:
    a viscometer having a heating cup;
    a pump in fluid communication with the heating cup, wherein the pump is configured to provide a flow of fluid from a fluid line inlet to the heating cup;
    a cleaning fluid tank in fluid communication with the heating cup, wherein the pump is configured to provide a flow of cleaning fluid from the cleaning fluid tank to the heating cup; and
    a system controller configured to provide instructions to the pump for controlling the flow of cleaning fluid from the cleaning fluid tanks to the heating cup.

2. The system of claim 1, further comprising:
    a heating element disposed proximate the heating cup; and
    a temperature controller electrically connected to the heating element and configured to control a temperature of the heating cup.

3. The system of claim 2, further comprising:
    a water supply tank; and
    a cooling jacket disposed proximate the heating cup and in fluid communication with the water supply tank.

4. The system of claim 1, wherein the system controller comprises a programmable logic controller.

5. The system of claim 1, wherein the system controller comprises instructions to control the viscometer to perform a rheology test.

6. The system of claim 1, wherein the system controller comprises instructions for the system to perform an automated cleaning sequence.

7. The system of claim 1, further comprising:
    a discharge port in fluid communication with the heating cup; and a discharge tank in fluid communication with the discharge port.

8. The system of claim 1, further comprising:
a return line in fluid communication with the return line inlet and a return line outlet;
wherein the return line is configured to circulate drilling fluid at a drilling location.

9. The system of claim 1, wherein the fluid comprises at least one of a group consisting of a drilling fluid, a slurry for cuttings re-injection, and a completion fluid.

10. The system of claim 1, wherein the system controller provides instruction to the system for automation of both testing and cleaning cycles.

11. A method for automated fluid monitoring at a drilling location, the method comprising:
providing automation controls for a fluid analyzer for controlling the automated fluid monitoring, the controls comprising instructions for:
introducing a fluid into a fluid analyzer, the fluid analyzer comprising a viscometer having a heating cup;
analyzing the fluid with the fluid analyzer, wherein the analyzing comprises determining fluid properties;
removing the fluid from the fluid analyzer;
introducing a cleaning fluid into the heating cup;
executing a cleaning operation; and
draining the cleaning fluid from the heating cup.

12. The method of claim 11, wherein the cleaning operation comprises:
actuating the viscometer, the actuating comprising:
rotating a bob of the viscometer; and
stirring the cleaning fluid in the heating cup.

13. The method of claim 11, wherein the analyzing comprises:
rotating a bob in the heating cup having a known volume of fluid; and
determining a torque required to rotate the bob in the fluid at a specified rotational speed.

14. The method of claim 11, further comprising:
outputting results of the analyzing.

15. The method of claim 14, wherein the results are output to at least one of a drilling management system, a visual display device, and an offsite monitoring station.

16. The method of claim 11, wherein the automation controls further comprise instructions for a demand cycle, the demand cycle comprising:
interrupting the automation cycle; and
actuating at least one of a demand analyzing operation and a demand cleaning operation.

17. The method of claim 11, wherein the fluid properties comprise a viscosity.

18. The method of claim 11, further comprising instructions for calibrating the fluid analyzer.

19. The method of claim 11, wherein the fluid comprises at least one of a group consisting of a drilling fluid, a slurry for cuttings re-injection, and a completion fluid.

20. The method of claim 11, wherein the system controller comprises at least one of a programmable logic controller and a computer.

21. The method of claim 11, wherein the system controller is controlled from an offsite location.

* * * * *